United States Patent [19]
Baerveldt et al.

[11] Patent Number: 5,397,300
[45] Date of Patent: Mar. 14, 1995

[54] GLAUCOMA IMPLANT

[75] Inventors: George Baerveldt, Pasadena; Larry W. Blake, Cott de Caza; George M. Wright, San Clemente, all of Calif.

[73] Assignee: Iovision, Inc., Irvine, Calif.

[21] Appl. No.: 231,988

[22] Filed: Apr. 21, 1994

Related U.S. Application Data

[63] Continuation of Ser. No. 157,333, Nov. 23, 1993, abandoned, which is a continuation of Ser. No. 867,995, Apr. 13, 1992, abandoned, which is a continuation-in-part of Ser. No. 531,010, May 31, 1990, Pat. No. 5,178,604.

[51] Int. Cl.6 ............................................. A61M 5/00
[52] U.S. Cl. ........................................ 604/8; 604/10
[58] Field of Search .................. 604/8, 9, 10, 27, 30, 604/43, 93, 128, 131, 149, 280, 294, 298; 623/4; 606/108

[56] References Cited

U.S. PATENT DOCUMENTS

| | | |
|---|---|---|
| 3,159,161 | 12/1964 | Ness . |
| 3,788,327 | 1/1974 | Donowitz et al. . |
| 3,860,008 | 1/1975 | Miner et al. . |
| 4,402,681 | 9/1983 | Haas et al. . |
| 4,428,746 | 1/1984 | Mendez . |
| 4,457,757 | 7/1984 | Molteno . |
| 4,521,210 | 6/1985 | Wong . |
| 4,722,724 | 2/1988 | Schocket . |
| 4,729,761 | 3/1988 | White . |
| 4,863,457 | 9/1989 | Lee . |
| 4,886,488 | 12/1989 | White . |
| 4,902,292 | 2/1990 | Joseph . |
| 4,915,684 | 4/1990 | MacKeen et al. . |
| 4,936,825 | 6/1990 | Ungerleider . |
| 4,946,436 | 8/1990 | Smith . |
| 4,968,296 | 11/1990 | Ritch et al. . |

FOREIGN PATENT DOCUMENTS

| | | |
|---|---|---|
| 102747 | 3/1984 | European Pat. Off. . |
| 168201 | 1/1986 | European Pat. Off. . |
| 2160778 | 1/1986 | United Kingdom . |
| 2187963 | 9/1987 | United Kingdom . |
| 906561 | 2/1982 | U.S.S.R. . |

OTHER PUBLICATIONS

"Intraocular Pressure", Alder, Alder's Physiology of the Eye, Chapter 5, pp. 249–277.

Bickford, "Molteno Implant System", Journal of Ophthalmic Nursing 7 Technology, 1987, vol. 6, No. 6, pp. 224–229.

Davidovski, "Long–Term Results with the White Glaucoma Pump–Shunt", Opthalmic Surgery, Apr. 1990, Vo. 21, No. 4, pp. 288–293.

Lee, et al., "Aqueous–Venous Shunt for Glaucoma", Arch Ophthalmol, vol. 99, Nov. 1981.

(List continued on next page.)

*Primary Examiner*—Sam Rimell
*Attorney, Agent, or Firm*—Knobbe, Martens, Olson & Bear

[57] ABSTRACT

An implant for use in the treatment of glaucoma is disclosed wherein the implant comprises an elastomeric plate having a non-valved elastomeric drainage tube attached thereto. The plate is elliptical in shape and curved so as to conform to the curvature of the eye. At least one hole is made in the plate to facilitate the formation of a tethered scar tissue bubble, referred to a bleb, to form around the carrier plate. The scar tissue will grow through the hole or holes and pull the perimeter of the bubble towards the carrier plate at the hole locations to tether the formation of the bleb to the carrier plate and finally to the sclera tissue. The plate is inserted into the eye in an incision made in the Tenon's capsule and sutured to the sclera. The drainage tube is tunnelled through the Tenon's capsule and cornea and inserted into the anterior chamber, thus providing patent fluid communication between the anterior chamber and the elastomeric plate. The flexible structure of the plate allows the plate to be easily inserted, thus reducing the surgical procedure length. In addition, the pliable material minimizes the risk of damage and trauma to surrounding tissues in the insertion process.

22 Claims, 4 Drawing Sheets

OTHER PUBLICATIONS

Minckler, et al., "Clinical Experience with the Single-plate Molteno Implant in Complicated Glaucomas", Ophthalmology, vol. 95, No. 9, Sep. 1988.

Motleno, "Use of Molteno implants to treat secondary glaucoma", Glaucoma, Grune & Stratton, Ltd., 1986.

White, "A New Implantable Ocular Pressure Relief Device", University of South Dakota Medical School, Sioux Falls, S.D.

"Experience with Motleno-type shunts", Ocular Surgery News, Jun. 1, 1989.

"Molteno Seton Implant", Brochure from Staar Surgical Company, Monrovia, Calif.

A. F. Yumagulova, Traslation of Russian Patent No. 906,561, issued on Feb. 23, 1992, pp. 1–4.

GLAUCOMA IMPLANT

RELATED APPLICATIONS

This application is a continuation of application Ser. No. 08/157,333, filed Nov. 23, 1993, abandoned, which is a continuation of application Ser. No. 07/867,995, filed on Apr. 13, 1992, abandoned, which is a continuation-in-part of application Ser. No. 07/531,010, filed May 31, 1990, now U.S. Pat. No. 5,178,604.

FIELD OF THE INVENTION

The invention relates to ocular implants, and, in particular, to an implant used in the treatment of glaucoma.

BACKGROUND OF THE INVENTION

Aqueous is a clear, colorless fluid that fills the anterior and posterior chambers of the eye. The aqueous is formed by the ciliary body in the eye and is a carrier of nutrients for the lens. In addition, the aqueous provides a continuous stream into which surrounding tissues can discharge the waste products of metabolism.

The aqueous produced in the ciliary processes circulates from the posterior chamber to the anterior chamber of the eye through the pupil and is absorbed through the trabecular meshwork, a plurality of criss-crossing collagen cords covered by endothelium. Once through the trabecular meshwork, the aqueous passes through Schlemm's canal and into venous circulation. The rate of aqueous outflow through the trabecular meshwork in a normal eye is typically 2.1 $\mu$L/min. Intraocular pressure in the eye is maintained by the formation and drainage of the aqueous. All the tissues within the corneoscleral coat covering the eyeball are subject to this pressure, which is higher than pressure exerted on tissues at other locations in the body.

Glaucoma is a progressive disease of the eye characterized by a gradual increase of intraocular pressure. This increase in pressure is most commonly caused by stenosis or blockage of the aqueous outflow channel, resulting in excessive buildup of aqueous fluid in the eyeball. Other causes include increase in venous pressure outside the eye which is reflected back through the aqueous drainage channels and increased production of aqueous. In a "normal" eye, intraocular pressure ranges from 4 to 12 mm mercury. In an eye with glaucoma, this pressure can rise to as much as 50 mm mercury. This increase in intraocular pressure produces gradual and permanent loss of vision in the afflicted eye.

Existing corrective methods for the treatment of glaucoma include drugs, surgery, and implants. Miotic drugs lower intraocular pressure by facilitating aqueous outflow. Beta blockers, epinephrine products, and carbonic anhydrase inhibitors which inhibit production of the aqueous, are also commonly used in pharmacological glaucoma treatment. Steroids have been used in long-term glaucoma treatment as well. However, pharmacological treatment is prohibitively expensive to a large majority of glaucoma patients. In addition, many people afflicted with the disease live in remote or undeveloped areas where the drugs are not readily accessible. The drugs used in the treatment, in particular the steroids, often have undesirable side effects and many of the long-term effects resulting from prolonged use are not yet known.

Surgical procedures have been developed in an effort to treat victims of glaucoma. An iridectomy, removal of a portion of the iris, is often used in angle-closure glaucoma wherein there is an occlusion of the trabecular meshwork by iris contact. Removal of a piece of the iris then gives the aqueous free passage from the posterior to the anterior chambers in the eye. A trabeculotomy, opening the inner wall of Schlemm's canal, is often performed in cases of open-angle glaucoma so as to increase the outflow of the aqueous, thereby decreasing intraocular pressure. While often successful, these surgical techniques possess inherent risks associated with invasive surgery on an already afflicted eye. Furthermore, the tissue of the eye can grow back to the preoperative condition, thereby necessitating the need for further treatment.

Ocular implants are often used in long-term glaucoma treatment without the disadvantages of drugs and invasive surgery. One such implant is disclosed in U.S. Pat. No. 4,457,757 entitled "Device for Draining Aqueous Humor" and commercially available as the Molteno ™ Seton Implant. The implant comprises a drainage tube connected to one or more ridged plate reservoirs. The reservoir plates are designed to conform to the curvature of the eye. A reservoir plate is placed under Tenon's capsule and sutured to the sclera. The drainage tube is implanted into the anterior chamber through a scleral flap. A second plate can be implanted under the superior rectus muscle and sutured to the sclera. At this point, the body will form a tissue around these plates. Increased pressure causes the tissues above the plates to lift and form a bleb into which aqueous fluid from the anterior chamber drains via the drainage tube. Once inside the bleb, the aqueous seeps into intercellular spaces and is removed by surrounding capillaries or lymphatics. This type of implant is disadvantageous as the plates are formed of a rigid plastic which makes insertion beneath the eye tissue difficult and time-consuming. Furthermore, the rigid material poses a risk of irritation and/or damage to adjacent vasculature and tissue.

U.K. Patent Application 2,160,778 entitled "Aqueous humor drainage device" discloses a similar type of implant device comprising a drainage tube and a drainage body. The tube is fixed to and opens directly onto a surface of the body. The device is sutured to the sclera of the eye and the tube positioned within the anterior chamber so as to provide outflow for the aqueous contained therein. The device further includes a pressure gradient limiting valve formed as a slit in the tube, however, this type of valve does not allow patent, i.e., open or two-way, flow through the drainage tube, thereby preventing retrograde aqueous flow into the anterior chamber.

Glaucoma implants require formation of scar tissue and a drainage bleb around the implant to control the outflow of the aqueous. In some cases, due to extreme intraocular pressure, the drainage bleb that forms is excessive in size, and may cause impaired vision due to unexpected complications. If the drainage bleb is too large, the eye may protrude from its orbit, or eye socket, and cause distortions in the patient's vision. This is especially problematic in patients with small orbits. In addition, the drainage bleb may press upon the internal tissues of the eye which will result in impaired vision due to increased retinal pressure. In these cases, the potential side effects may negate the advantages of the surgery.

SUMMARY OF THE INVENTION

The present invention provides an implant for the treatment of glaucoma which can be easily inserted into an afflicted eye and which provides for patent flow between the implant and the anterior chamber of the eye and reduces the complications caused by excessive drainage bleb formation. The implant comprises a single plate formed of a pliable, elastomeric material having a non-valved tube attached to and opening onto the upper surface of the plate. The pliable plate is sutured to the sclera and covered by a thick flap of Tenon's capsule so as to be encapsulated within the drainage bleb. The attached tube is tunneled out through Tenon's capsule and in through the limbus so as to provide a drain for aqueous fluid. The exposed portion of the tube is covered by a scleral graft. Because of the pliable construction and shape, the device can be implanted much quicker than previously realized with other implants. This substantially shortens the time required to perform the surgical procedure. Further, at least one hole is positioned centrally in the plate of the glaucoma implant and sized to allow for growth of scar tissue through each hole. Desirably, a single hole is positioned and sized to allow the growth of scar tissue. More preferably, a plurality of holes are positioned and sized to allow the growth of scar tissue through each hole. The formation of the scar tissue pulls the perimeter of the drainage bleb towards the plate of the implant forming a scar tissue tether in the drainage bleb which reduces the overall height of the bleb. The reduction in size of the drainage bleb helps to overcome complications such as protrusions of the eye from the orbit and pressure on the internal tissues of the eye both resulting in impaired vision.

In a further aspect of the present invention a method of treating glaucoma in an eye, using the elastomeric implant of the present invention is disclosed. The method comprises the following steps. First, an incision is made in Tenon's capsule of the eye. Next, the elastomeric plate of the implant is inserted beneath Tenon's capsule and above the sclera to form a bleb. The drainage tube is positioned within the eye so as to provide fluid communication between the eye and the elastomeric plate. Finally, the bleb is tethered to limit its height. The bleb is tethered by growing scar tissue through a central hole in the elastomeric plate. The scar tissue once it grows through the central hole attaches itself to said sclera to further tether the height of the bleb.

In a unique aspect of the invention, the plate is constructed so as to be radio-opaque. This allows the implant to be easily viewed by X-ray after surgery, advantageously allowing progress monitoring. A suture is placed around the drainage tube and knotted to close off the tube and prevent initial flow between the anterior chamber and elastomeric plate. Once bleb tissue formation is complete the suture is removed in a second surgical procedure. Alternatively, a dissolving suture can be used to secure the drainage tube. In addition, the device includes a dissolving plug contained within the drainage tube. The plug prevents the drainage of aqueous fluid until formation of the bleb is completed. Once bleb formation has occurred, the plug dissolves, allowing for unrestricted flow between the anterior chamber and bleb.

Additional alternative embodiments of the implant are disclosed wherein the number of holes in the plate are increased to provide multiple tethering points to further limit the height of the bleb.

DETAILED DESCRIPTION OF THE INVENTION

Figure 1:
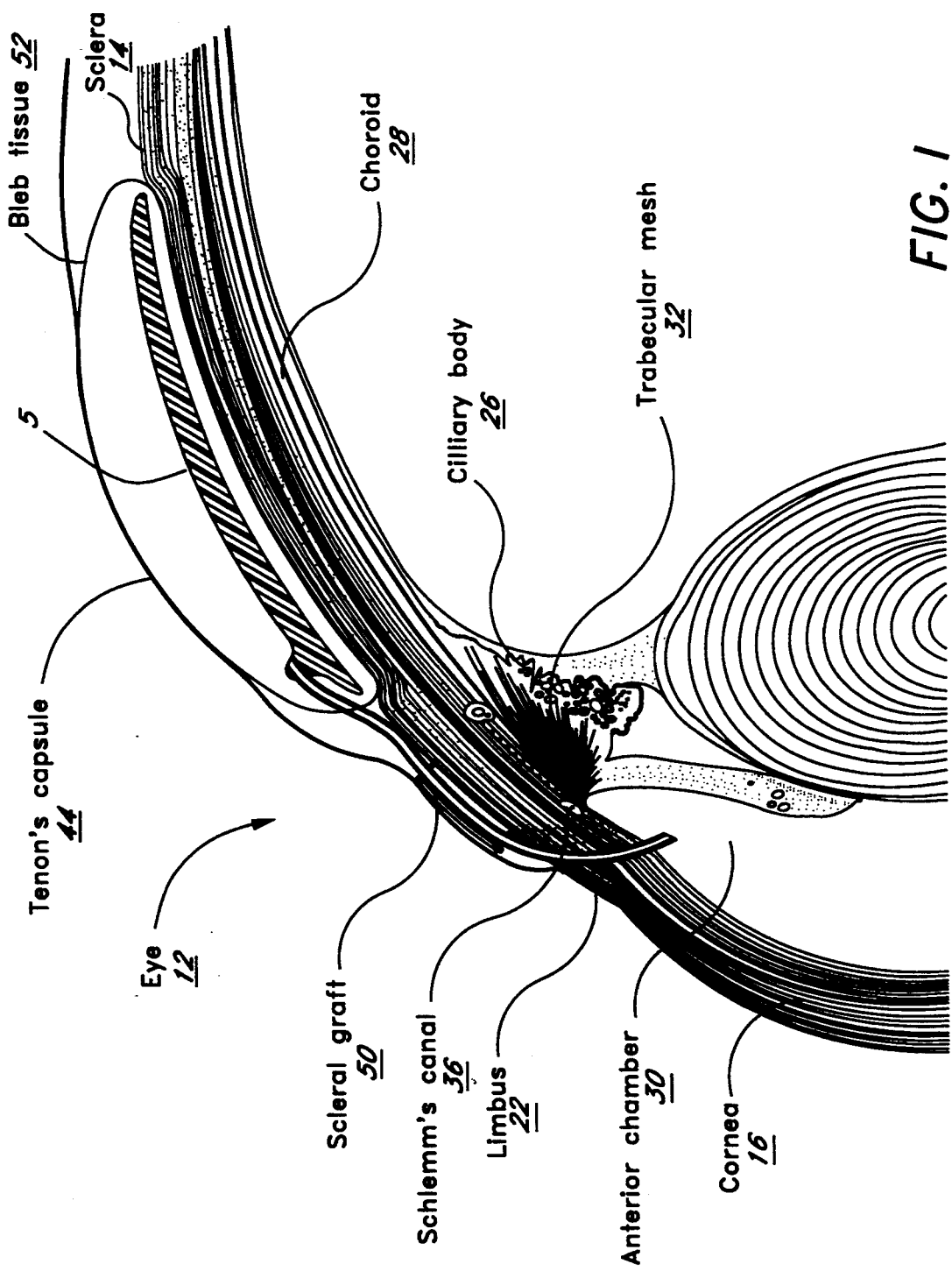
FIG. 1 is a sectional view taken vertically through the upper, frontal portion of the eye, illustrating our prior glaucoma implant in a human eye.
Figure 2:
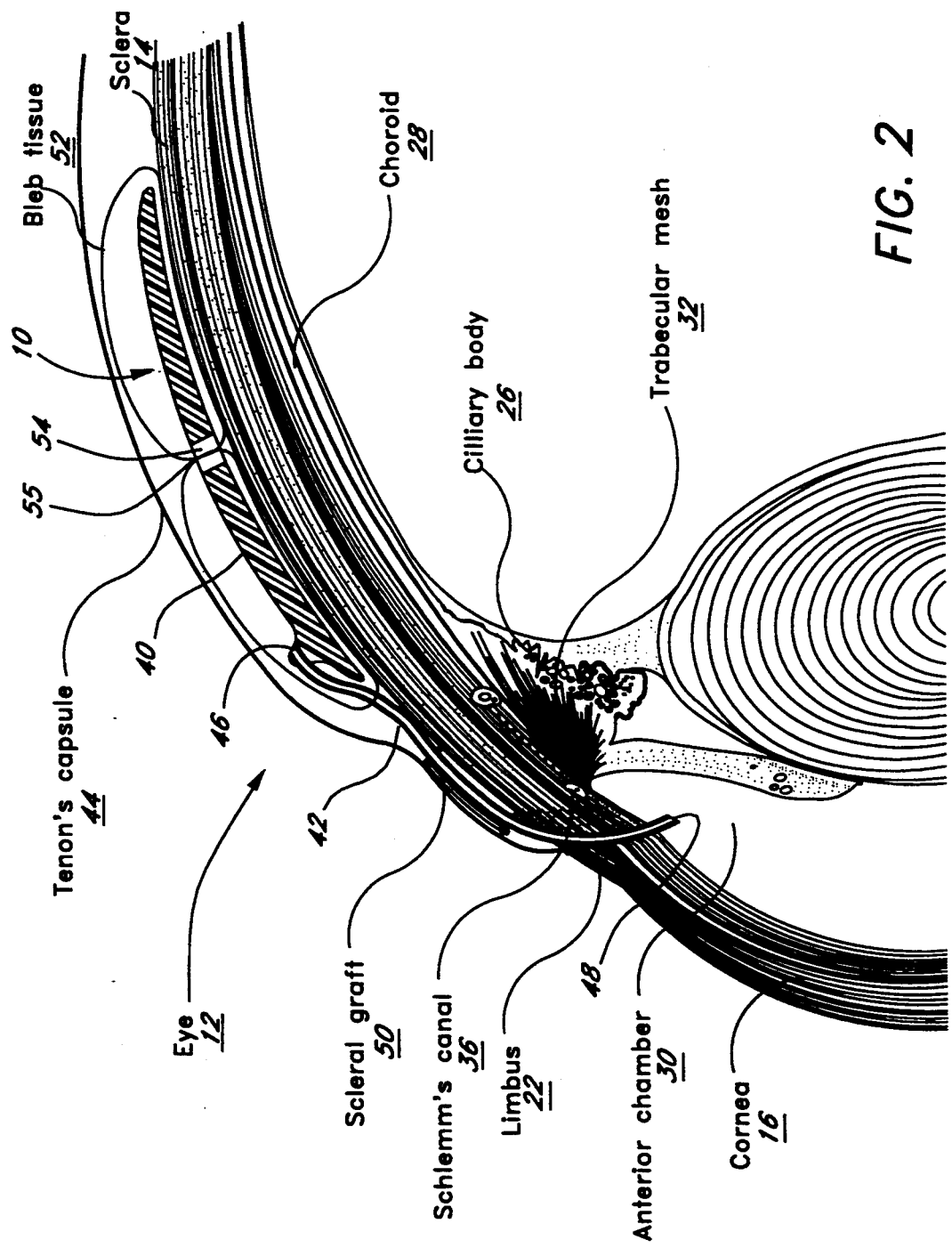
FIG. 2 is a sectional view taken vertically through the upper, frontal portion of the eye, illustrating the present invention implanted in a human eye.
Figure 3:
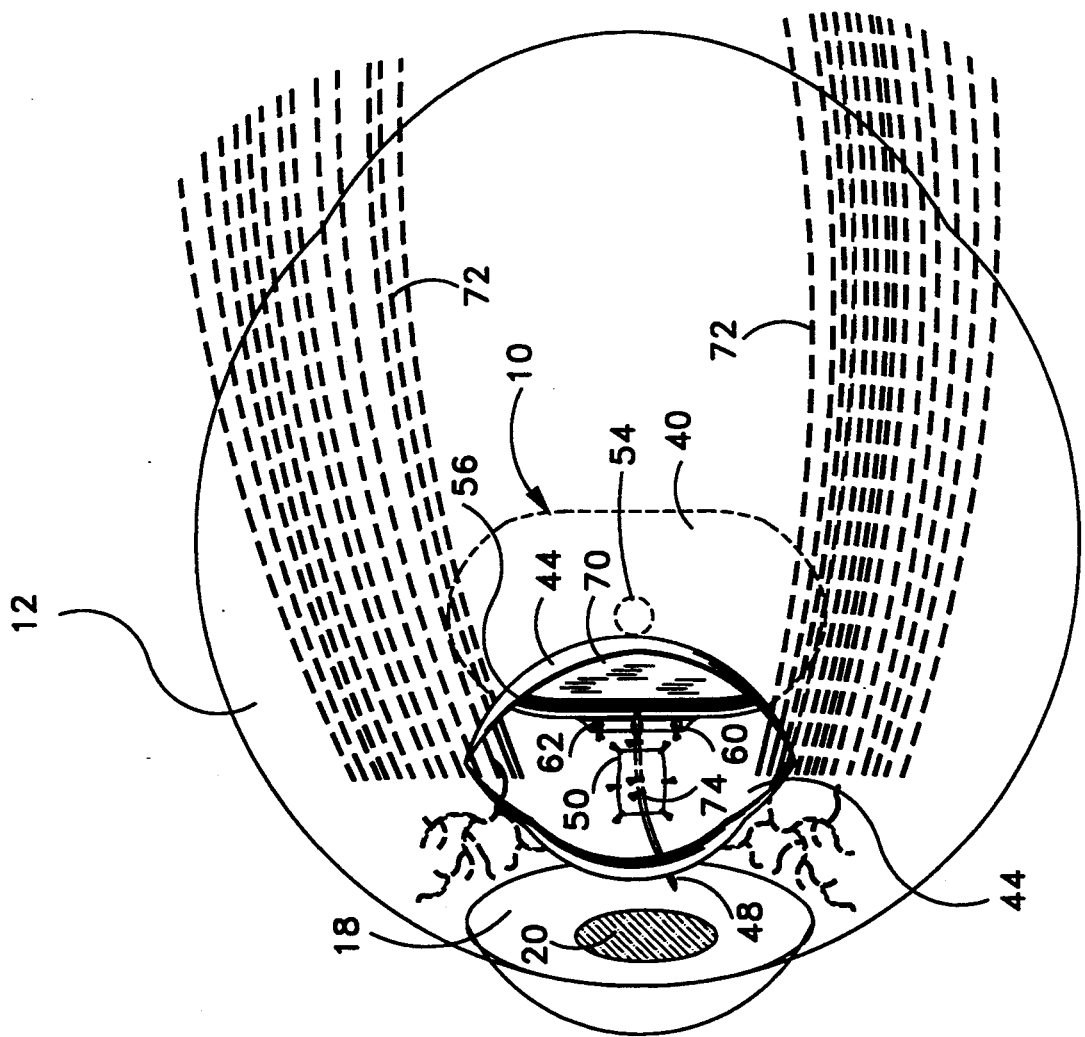
FIG. 3 is a schematic, perspective view of the eye, illustrating the present invention implanted in a human eye.

FIG. 1 illustrates our prior implant 5 positioned within an eye 12. FIGS. 2 and 3 illustrate an implant 10 constructed in accordance with the present invention positioned within the tissue of an eye 12. The relevant structure of the eye 12 will be described briefly below so as to provide background for the anatomical terms incorporated herein, however, it should be realized that several anatomical details have been omitted for clarity of understanding. The tough outer membrane known as the sclera 14 covers all of the eye 12 except that portion covered by the cornea 16, the thin, transparent membrane which covers the iris 18 and the pupil 20. The cornea 16 merges into the sclera 14 at a juncture referred to as the limbus 22. The ciliary body 26 begins at the limbus 22 and extends along the interior of the sclera 14 and becomes the choroid 28. The choroid 28 is a vascular membrane which extends along the retina back toward the optic nerve. The eye sits within a bony cavity in the skull referred to as an eye socket or orbit.

It is well-known that aqueous is produced by the ciliary body 26 and reaches the anterior chamber 30 formed between the iris 18 and the cornea 16 through the pupil 20. In a normal eye, the aqueous is removed through the trabecular meshwork 32. There the aqueous passes through Schlemm's canal 36 and through veins which merge with blood-carrying veins and into venous circulation. Intraocular pressure is maintained in the eye 12 by the intricate balance of secretion and absorption or outflow of the aqueous in the manner described above. Glaucoma results from excessive buildup of aqueous fluid in the anterior chamber 30 which produces an increase in intraocular pressure.

The present invention is designed for treatment of glaucoma by facilitating the outflow of the aqueous in the anterior chamber 30 of the eye 12. The implant 10 comprises a pliable carrier plate 40 connected to a drainage tube 42. As illustrated in FIGS. 2 and 3, the carrier plate 40 is implanted in the eye 12 beneath a layer of Tenon's capsule 44 and sutured to the sclera 14. The discharge tube 42 comprises a first end 46 a second end 48 wherein the first end 46 is attached to the plate 40. The second end 48 of the tube 42 extends through the layer of Tenon's capsule 44 and through the cornea 16 into the anterior chamber 30 of the eye 12. A scleral graft 50 covers the exposed portion of the tube 42 located between the Tenon's capsule 44 and the cornea 16. A large drainage bleb 52 surrounds the carrier plate 40 and lifts the layer of Tenon's capsule 44 above the sclera 14.

As illustrated in FIG. 1, in some cases of extremely high intraocular pressure, a large drainage bleb 52 may form. When the drainage bleb 52 becomes large, pressure is placed on the eye tissue and causes various problems. In some of these cases, the large bleb 52 may shrink over time as the intraocular pressure decreases, and the surrounding scar tissue matures. In other cases where the patient's orbits' are small, the problem can be more long term. The present invention, illustrated in FIG. 2, adds a small hole 54 in the center of the carrier plate 40 of the glaucoma implant 10. The scar tissue will grow through the hole 54 and form a tether. The scar tissue tether will then attach itself to the sclera 14. This scar tissue growth through the hole 54 will reduce the size of the drainage bleb 52 on both sides of the carrier plate 40 by pulling the perimeter of the bleb 52 towards the plate, and forming a dimple 55 in the center of the bleb 52. The decreased size of the newly tethered drainage bleb 52 will reduce the overall pressure against the eye tissues on both sides of the plate 40, thus reducing the possibilities of vision impairment. In addition, the scar tissue will grow through the hole 54 in the implant 10 and anchor the drainage bleb 52 and plate 40 close to the sclera 14 to prevent any protrusion problems into the orbit of the eye 12.

Figure 4:
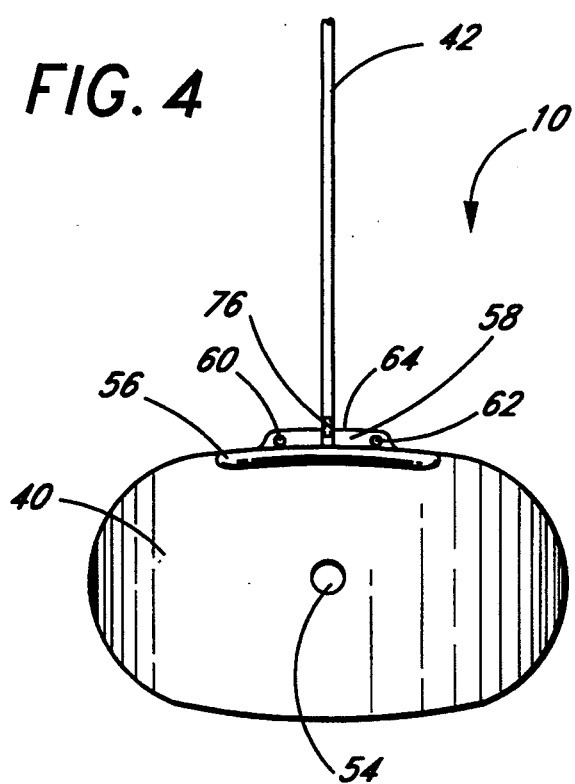
FIG. 4 is a perspective views illustrating the implant of the present invention.

The preferred embodiment of a single holed implant 10 is shown in more detail in FIG. 4. The carrier plate 40 is generally spherical in shape, and has a perimeter which is elliptical. The surface area of the plate 40 is preferably in the range of 100 to 600 mm$^2$ depending on glaucoma condition and the radius of curvature of the plate is preferably 12 to 14 mm. The thickness of the plate 40 is preferably in the range of 0.5 to 2.0 mm. A small hole 54 with a diameter preferably between 50 microns and 10 mm is centrally located anywhere outside of a 500 micron distance from any edge of the implant 10 to facilitate a tethered bleb formation. More preferably, the hole 54 is 800 microns in diameter. In the single holed embodiment illustrated in FIG. 4, the hole 54 is preferably formed in the center of the carrier plate to provide the greatest reduction in the size of the bleb. The carrier plate 40 includes a raised ridge 56 formed adjacent one of the larger-radius perimeter edges of the ellipse, on the convex spherical surface. The rounded edge of the plate 40 extending on either side of the raised ridge 56, not including that portion of the plate 40 adjacent the ridge 56, is entirely radiused, tapered, and blended so as to facilitate insertion as described below. The inner surface of the carrier plate 40 is concave so as to conform to the curvature of the eye 12 and the curvature of the ridge 56 matches the curvature of the sclera 14. An extension 58 of the carrier plate 40 is formed adjacent the ridge 56 and includes two small suture holes 60, 62. The suture holes 60, 62 allow the carrier plate 40 to be held in position in the eye 12 as the drainage bleb 52 forms. The growth of scar tissue in the suture holes 60, 62 is blocked by the suture material, therefore these suture holes 60, 62 do not have the same bleb reducing effect as the hole 54 in the main body of the carrier plate. Further, the suture holes 60, 62 are located on the posterior perimeter of the carrier plate 40 which is within the 500 micron distance limit from the perimeter of the implant 10, and thus renders these hole ineffective in the reduction of the bleb 52 size. If scar tissue was able to form within these suture holes 60, 62, the reduction in the size of the bleb 52 would not be significant enough, as the dimple 55 in the bleb 52 would be formed at the perimeter, and the main portion of the drainage bleb would still be large enough to cause the above discussed complications.

The drainage tube 42 is connected to the carrier plate 40 with adhesive, such as Clear Silicone Rubber Adhesive RTV-118 manufactured by General Electric Silicone Products of Waterford, N.Y., via a small hole 64 formed in the ridge 56 and is bonded to the plate 40 using well-known bonding techniques. The first end of the tube 46 thus drains into the recess formed at the junction of the ridge 56 and the smooth outer surface of the carrier plate 40. The plate 40 is preferably formed of silicone elastomer, such as SILASTIC ™, Medical Grade Q7-4765, 65 Shore A, manufactured by Dow Corning Corporation of Midland, Mich., although other silicone elastomers in the range of 40–85 Shore A and having good elastic memory are also suitable. The silicone elastomer is filled with a radiopaque material, such as Barium Sulfate, so that the implant is visible in X-ray procedures, thereby allowing patient progress monitoring. The drainage tube 42 is preferably a 1.0 to 3.0 French flow tube, approximately 10 mm in length, formed of SILASTIC ™, Medical Grade RX-50, also available from Dow Corning Corporation.

The present invention can be implanted using known ophthalmological surgical techniques and, with reference to FIGS. 2–4, the surgical implant procedure will be briefly described. An initial incision 70 is made in the Tenon's capsule 44 proximal the limbus 22. The carrier plate 40 is inserted through this incision 70 and positioned beneath the Tenon's capsule 44 and a portion of the rectus muscle 72, thus covering the sclera 14. The carrier plate 40 can be sutured to the sclera 14, or alternatively, to the rectus muscle 72 if a larger implant 10 is used, with the suture holes 60, 62. The drainage tube 42 is tunneled out through the Tenon's capsule 44 and in through the limbus 22 such that the second end 48 of the tube 42 extends into the anterior chamber 30 of the eye 12. The exposed portion of the drainage tube 42 is then covered with the scleral graft 50. The drainage tube 42 is sutured closed with a suture(s) 74 to prevent any drainage of aqueous prior to formation of the bleb tissue 52 over the carrier plate 40.

The formation of the bleb 52 occurs in response to the introduction of the carrier plate 40 into the tissue of the eye 12. The bleb 52 comprises a thin layer of connective tissue which encapsulates the carrier plate 40, thus lifting the Tenon's capsule 44 above the sclera 14 as shown. Typically, bleb formation occurs in the range of 2 to 8 weeks postoperatively, at which time additional surgery can be performed to remove the suture 74 and allow flow of aqueous from the anterior chamber 30 to the bleb 52 via the drainage tube 42. Alternatively, a dissolving suture can be used to seal the drainage tube 42. Further, a dissolving plug 76 can be placed in the drainage tube 42 to ensure that the majority of aqueous flow does not begin until formation of the bleb 52 is complete. The dissolving plug 76 is preferably formed of Poly Vinyl Alcohol (PVA), Poly Vinyl Pyrolidone (PVP), enzymatically activated collagen, or other biomedically suitable materials which slowly dissolve, thus gradually permitting the flow of aqueous and relieving intraocular pressure. After removal or dissolution of the suture 74 or dissolving plug 76 blocking the drainage tube 42, the aqueous flow between the tube 42 and bleb 52 is advantageously a patent flow, allowing for both flow from the anterior chamber 30 to the bleb 52 and vice versa. This ensures that retrograde flow from the bleb 52 to the anterior chamber 30, occurring in response to pressure on the eye 12 from the outside, for example, when the lid is forced closed or when the eyeball is pressed on with a finger, does not adversely or harmfully affect intraocular pressure within the eye 12. The fluid contained in the bleb 52 seeps through the bleb into intracellular spaces within eye 12 and is then removed through surrounding capillaries or lymphatics.

The flexible, elastomeric material used to form the present invention and its elliptical shape allow the implant 10 to be inserted much more easily than previously realized with other glaucoma treatment implants. During the insertion process, the carrier plate 40 can be "folded" in half about the axis of the tube 42 and then inserted through the incision 70. Once placed through the incision 70, the carrier plate 40 will return to its original shape and can be positioned so as to cover the sclera 14, as described above. Further, the material from which the plate 40 is formed is soft and pliable, which results in much less trauma and irritation to the surrounding tissues and vasculature than experienced with a rigid plate device. In addition, since the plate 40 is folded, a smaller incision can be made in the Tenon's capsule 44. Thus, the pliable carrier plate 40 significantly decreases the surgical procedure length while also minimizing tissue and vasculature damage which can occur in the insertion process.

Figure 5:
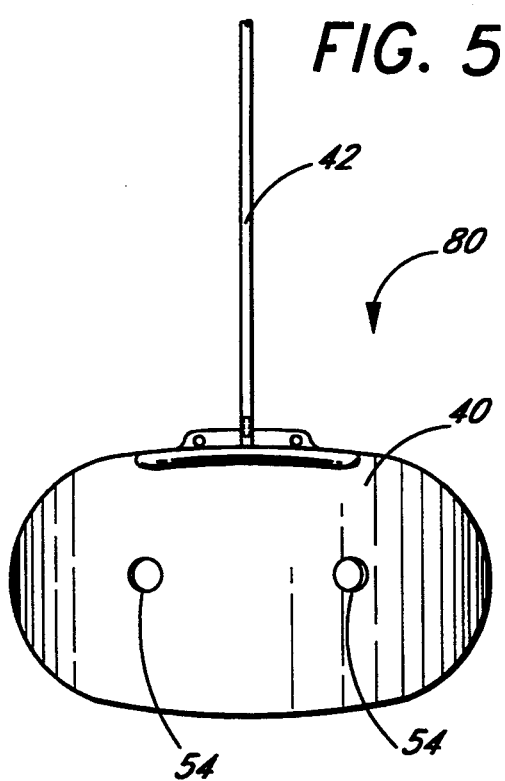
FIG. 5 is an alternative embodiment of the present invention.

An alternative embodiment of the present invention is illustrated in FIG. 5. FIG. 5 illustrates an implant with two holes 54 formed in the carrier plate 40. The holes 54 are once again between 50 microns and 10 mm in diameter, and are preferably placed in horizontal alignment across the surface of the plate 40. As the number of holes 54 in the corner plate 40 increases, preferably the diameter of the holes 54 decreases proportionally, but remain within the above range of preferable diameters. In this embodiment, the holes 54 will facilitate the formation of two dimples 55 in the tissue of the drainage bleb 52. Thus, the overall height of the bleb 52 in both the upper and lower directions will be significantly decreased as the bleb 52 is pulled toward the carrier plate 40 at both of the hole 54 locations.

Figure 6:
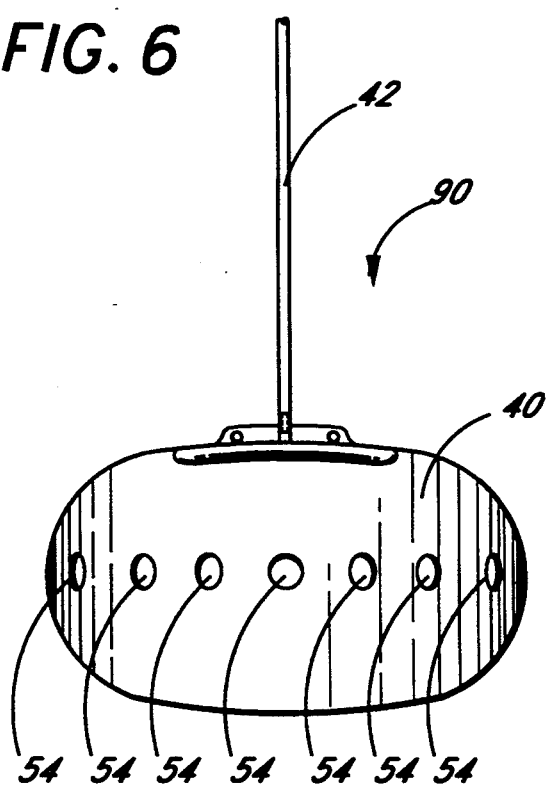
FIG. 6 shows an additional alternative embodiment of the present invention.

Another alternative embodiment of the present invention is illustrated in FIG. 6. FIG. 6 illustrates an implant 90 with essentially the same shape as the embodiments illustrated in FIGS. 4-5, with the addition of a plurality of horizontally aligned holes 54 in the carrier plate 40. Each of the holes 54 will form a dimple 45 in the drainage bleb 52 by permitting scar tissue growth through each of the holes 54, thus decreasing the overall height of the bleb 52. As the number of holes increases in the carrier plate 40, the number of dimples 55 in the resulting drainage bleb 52 will increase proportionately until the horizontal area of the carrier plate 40 and the diameter of the holes 54 limit the addition of other holes 54.

Although the invention has been described with reference to specific embodiments, the description is intended to be illustrative of the invention and is not intended to be limiting. Various modifications and applications may occur to those skilled in the art without departing from the true spirit and scope of the invention as defined in the appended claims.

What is claimed is:

1. An implant for draining aqueous fluid from an eye, comprising:

a thin, elastomeric plate having first and second surfaces joined at the plate perimeter, said perimeter of said plate being elliptical, said first and second surfaces curved spherically to conform to the curvature of said eye;

at least one through hole positioned centrally in said plate and passing through said plate from said first surface to said second surface and sized to allow growth of scar tissue through said hole; and an elastomeric drainage tube attached to said plate, said drainage tube comprising a first and a second open ends, said first end open onto one of said first and second surfaces of said elastomeric plate and wherein said second end extends for connection with said eye to provide fluid communication between said eye and said one of said first and second surfaces of said elastomeric plate.

2. The implant defined in claim 1, wherein said elastomeric plate further comprises a raised ridge extending from one of said first and second surfaces and having an aperture formed therein, said drainage tube bonded to said aperture formed in said ridge.

3. The implant defined in claim 1, further including first and second apertures formed in said elastomeric plate, wherein said first and second apertures provide first and second suture locations to attach said elastomeric plate to said eye.

4. The implant as defined in claim 1, wherein said elastomeric plate and said elastomeric drainage tube are formed of silicone elastomer.

5. The implant as defined in claim 4, wherein said silicone elastomer of said plate has hardness in the range of 40 to 85 Shore A.

6. The implant as defined in claim 1, wherein the surface area of said plate is in the range of 100 to 600 mm$^2$.

7. The implant as defined in claim 1, wherein said drainage tube includes a dissolving plug positioned therein, said dissolving plug for controlling said flow between said eye and one of said first and second surfaces of said elastomeric plate.

8. The implant as defined in claim 1, wherein said plate comprises a plurality of centrally positioned and sized through holes to allow the growth of scar tissue through said holes.

9. The implant as defined in claim 1, wherein said plate comprises a single centrally positioned though hole sized to be completely filled with scar tissue.

10. The implant as defined in claim 1, wherein said at least one through hole has a diameter between 50 microns and 10 mm.

11. The implant as defined in claim 10, wherein said at least one through hole has a diameter of 800 microns.

12. The implant as defined in claim 1, wherein said at least one through hole is positioned within at least 500 microns from a perimeter of said implant.

13. The implant as defined in claim 1, wherein said implant enables the growth of scar tissue around said plate to form a drainage bleb with at least a dimple formed in said bleb at the location of said hole.

14. A method of treating glaucoma, using an implant comprising an elastomeric plate attached to an elastomeric drainage tube, wherein said elastomeric plate further comprises a first surface, a second surface, and at least one centrally located through hole passing through said plate from said first surface to said second surface sized to be completely filled with scar tissue, comprising the steps of:

making an incision in the Tenon's capsule of an eye;
inserting said elastomeric plate beneath said Tenon's capsule and above the sclera to cause the formation of a bleb around said elastomeric plate;
conducting the growth of scar tissue near either said first or said second surfaces through said at least one centrally located though hole to limit the height of the bleb; and
positioning said drainage tube so as to provide fluid communication between said eye and said elastomeric plate.

15. The method of claim 14, wherein said growth of scar tissue through said at least one centrally located through hole attaches said scar tissue of said bleb through said at least one centrally located through hole to said sclera.

16. A device for the treatment of glaucoma in an eye, comprising:
a thin, elastomeric plate having inner and outer surfaces with a spherical surface contour conforming to the curvature of said eye;
at least one through hole positioned centrally in said plate connecting said inner and said outer surfaces and sized to allow growth of scar tissue through said hole; and
an elastomeric drainage tube attached to said plate having first and second open ends with a first end open onto said surface and extending for connection with said eye to provide a fluid passage between said eye and said surface of said elastomeric plate.

17. An implant for the treatment of glaucoma in an eye, comprising:
a thin, elastomeric plate, said plate having inner and outer surfaces and a surface area which forms an ellipse;
at least one through hole positioned centrally in said plate connecting said inner and outer surfaces and sized to allow growth of scar tissue through said hole; and
an elastomeric drainage tube attached to said plate, said drainage tube comprising first and second open ends with a first end open onto the surface of said plate and a second end extending for communication with said eye to provide fluid communication between said eye and said surface of said plate.

18. An implant for draining aqueous fluid from an eye, comprising:
a thin elastomeric plate having first and second surfaces joined at a raised ridge, wherein the surface area of said plate is elliptical and wherein said first and second surfaces are curved spherically so as to conform to the curvature of said eye, said elastomeric plate positioned within a bleb formed between the sclera and the Tenon's capsule of said eye;
at least one through hole positioned centrally in said plate and connecting said first and second surfaces to form a dimple in said bleb by formation of a scar tissue tether in said hole; and
an elastomeric drainage tube attached to said raised ridge, said drainage tube comprising first and second open ends a first end open onto one of said first and second surfaces of said elastomeric plate and a second end extending into the anterior chamber of said eye, thereby providing fluid communication between said anterior chamber and said bleb.

19. The implant as defined in claim 18, wherein one of said first and second surfaces includes at least one aperture to suture said elastomeric plate to said sclera.

20. The implant as defined in claim 18, wherein said elastomeric plate is radio-opaque.

21. An implant for placement between a first layer of eye tissue and a second layer of eye tissue for draining fluid from an eye, comprising:
a thin elastomeric plate having a first upper and second lower surfaces joined at the plate perimeter and conforming to the curvature of said eye;
at least one hole passing from said first surface to said second surface, positioned centrally in said plate and sized for allowing said first and second eye tissue layers to join by formation of a scar tissue tether through said hole;
an elastomeric drainage tube attached to said plate, said drainage tube comprising first and second open ends, said first end open to one of said first and second surfaces of said plate and said second end for connection to said eye to provide fluid communication between said eye and said plate.

22. The implant as defined in claim 1, wherein said elastomeric plate is radio-opaque.

* * * * *